United States Patent [19]

Kaplan et al.

[11] 4,096,863
[45] Jun. 27, 1978

[54] BAND FOR ANCHORING A CATHETOR OR ANY OTHER TUBULAR DEVICE TO THE BODY

[75] Inventors: David Kaplan; Irving Brezack, both of Sharon, Mass.; Nathan H. Young, deceased, late of Boynton Beach, Fla.; by David Kaplan, executor; by Irving Brezack, executor, both of Sharon, Mass.; Herbert H. Wapner, Canton, Mass.

[73] Assignee: Baka Manufacturing Company, Inc., Plainville, Mass.

[21] Appl. No.: 745,804

[22] Filed: Nov. 29, 1976

Related U.S. Application Data

[63] Continuation-in-part of Ser. No. 612,364, Sep. 11, 1975, abandoned.

[51] Int. Cl.² .............................................. A61M 25/02
[52] U.S. Cl. ...................... 128/349 R; 128/DIG. 26; 24/16 R; 224/5 H
[58] Field of Search ............... 128/348, 349 R, 350 R, 128/351, DIG. 26, DIG. 15, 165, 169, 134; 24/16 R, 81 CC, 81 SK, 204; 224/5 R, 5 H

[56] References Cited

U.S. PATENT DOCUMENTS

| 3,000,384 | 9/1961 | Piers .................................. 132/46 R |
| 3,480,012 | 11/1969 | Smithers et al. ........... 128/DIG. 15 |
| 3,536,068 | 10/1970 | Stubbs .................................. 128/134 |
| 3,640,273 | 2/1972 | Ray ...................................... 128/87 |
| 3,706,310 | 12/1972 | Garnett ................................ 128/94 |
| 3,726,280 | 4/1973 | Lacount .......................... 128/349 R |
| 3,878,849 | 4/1975 | Muller et al. ................... 128/349 R |
| 3,947,927 | 4/1976 | Rosenthal ........................... 24/16 R |

*Primary Examiner*—Dalton L. Truluck
*Attorney, Agent, or Firm*—Wolf, Greenfield & Sacks

[57] ABSTRACT

A band for securing a catheter or similar device to a limb of a human comprising a stretchable primary strap adapted to encircle the limb. A part of the strap is made of a soft looped fabric and the strap also carries a male Velcro-type fastening material which cooperates with the looped fabric to enable the strap to be secured in place about the limb. A secondary strap made of a flexible material is secured at one end intermediate the ends of the primary strap. That end of the secondary strap also carries a clip having an eye. The other end of the secondary strap, made of a male Velcro-type fastening material, may be threaded through the eye of the clip and engage the looped fabric so that the secondary strap forms a closed loop for encircling the catheter or similar device and holding it securely in place on the limb.

13 Claims, 8 Drawing Figures

4,096,863

BAND FOR ANCHORING A CATHETOR OR ANY OTHER TUBULAR DEVICE TO THE BODY

RELATED APPLICATION

This application is a continuation-in-part of copending application Ser. No. 612,364, filed Sept. 11, 1975, now abandoned.

INTRODUCTION AND BACKGROUND

This invention relates to a new and improved band for securing catheters and similar devices to the limb of a human. More particularly, this invention comprises an improvement over the devices shown in U.S. Pat. Nos. 3,765,421 and 3,878,849.

There are presently a number of devices on the market for securing catheters and similar devices to a limb. These devices perform a very useful function. They are both a convenience to the attendant applying the device to the patient and a comfort to the patient. The present invention is intended to improve the performance of such devices.

One important object of this invention is to provide a band of the class described which is infinitely adjustable in size both with respect to the size of the limb to which it is to be attached and to the size of the member which it is to support.

Another important object of this invention is to provide a band of the class described which is very simple to manufacture and easy to apply.

Still another object of this invention is to provide a band of the class described, which is comfortable when worn and remains in place on the limb until intentionally removed.

Yet another important object of this invention is to provide a catheter band that enables the attending doctor or nurse to apply catheter traction to the device and that discourages self removal of the drain tube.

And yet another important object of the invention is to provide a locking device for catheters that permits visual inspection of the drain tube while in the locked position.

To accomplish these and other objects, the band of this invention includes a primary strap made of a stretchable section and a non-stretchable section attached end to end and adapted to encircle the limb to which it is to be attached. The non-stretchable section carries a looped material on its outer surface which together with a male Velcro-type fastening material at the free end of the stretchable section provides means for closing the strap about the limb. A secondary strap made of a male Velcro-type fastening material is secured to the primary strap and carries a clip at one end through which the other end of the strap itself may be threaded to form a closed loop about the catheter or other device to be anchored to the limb. The Velcro material of the secondary strap cooperates with the looped material forming part of the primary strap for locking the secondary strap closed about the catheter.

These and other objects and features of this invention will be better understood and appreciated from the following detailed description of two embodiments thereof, selected for purposes of illustration and shown in the accompanying drawing.

BRIEF FIGURE DESCRIPTION

DETAILED DESCRIPTION

The band shown in FIGS. 1-4 is illustrated as it may support a catheter tube T to the thigh of a patient's leg. The band includes a primary strap 10 and a secondary strap 12 shown in detail in FIGS. 2 to 4.

Figure 1:
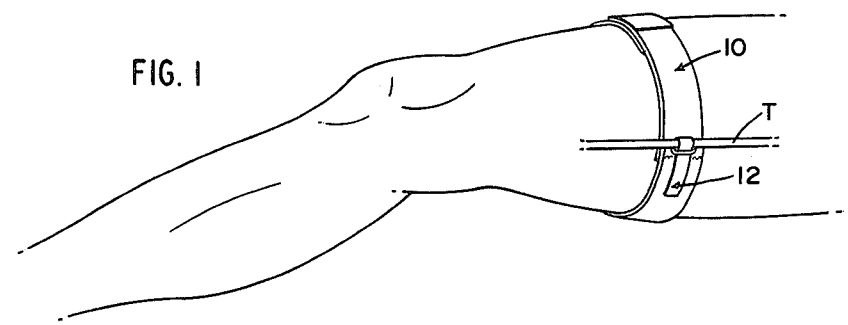
FIG. 1 is a fragmentary perspective view of a leg of a human, to which one embodiment of this invention is secured and suggesting the manner in which the band retains a catheter along the leg.
Figure 2:
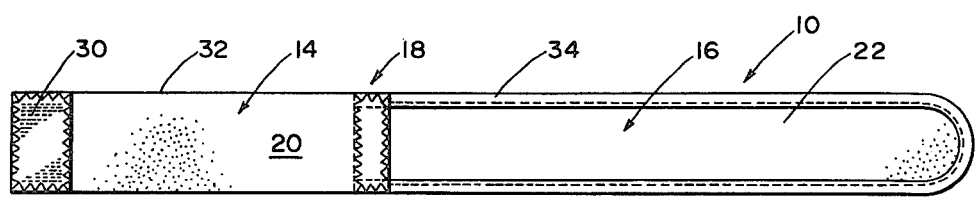
FIG. 2 is a plan view of the inner surface of the band shown in FIG. 1
Figure 3:
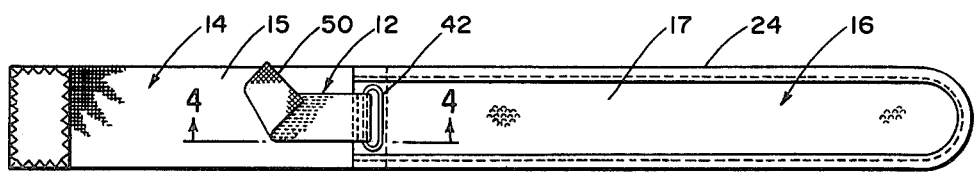
FIG. 3 is a plan view of the outer surface of the band shown in FIG. 1
Figure 4:
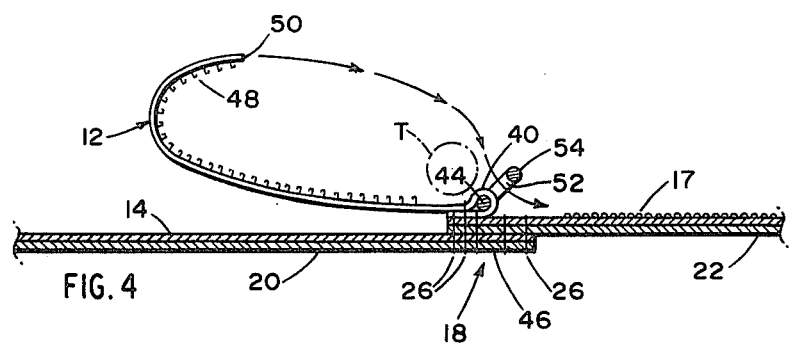
FIG. 4 is a fragmentary cross sectional view taken along the section line 4—4 of FIG. 3 and showing the secondary band which holds the catheter or similar device in locked position.
Figure 5:
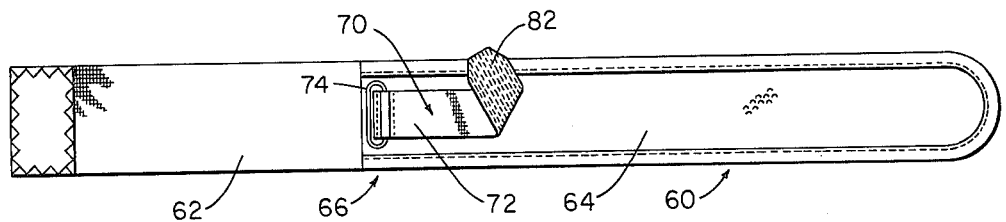
FIG. 5 is a view similar to FIG. 3 and showing a second, preferred embodiment of this invention.
Figure 6:
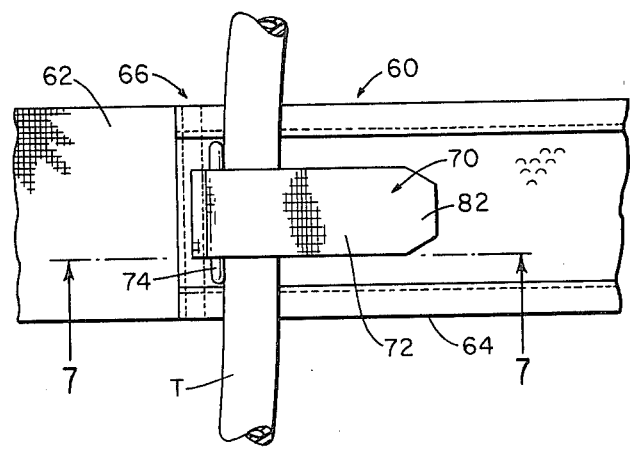
FIG. 6 is an enlarged fragmentary plan view of the embodiment shown in FIG. 5 as used to retain a catheter in locked position.

The primary strap 10 is made in two sections 14 and 16 secured end to end as suggested at 18 in FIGS. 2 to 4. Section 14 is made of an elastic webbing material 15 which is stretchable in a lengthwise direction but is of a relatively fixed dimension across its width. The inside surface of the webbing carries a soft lining material 20 which may be in the form of a Helenca backing or some other soft material which is comfortable to the skin but which does not interfere with the elasticity of webbing 15. The section 16 includes an inexpensive non-stretchable fabric 17 made of a looped material typically woven of cotton of the velvet type, and the loops extend outwardly from the outer face of section 16, that is the surface seen in FIG. 3. In the preferred form, section 16 also includes a soft lining material 22 which lies against the skin when the band is applied to the body. A binding 24 is stitched about the edge of section 16 to prevent fraying of the material 17 or its lining 22 along the edges.

A pair of parallel rows of stitching 26 are suggested in FIG. 4, to secure the overlapped adjacent ends of sections 14 and 16 together. Typically, section 16 about 12 inches in length, and the band is of uniform width, approximately two inches wide.

A small piece of male Velcro-type fastening material 30 is stitched to the inner or lining side of section 14 at its free end 32 with the hook-like barbs of the Velcro facing away fron the lining. When the primary strap 10 is wound about the limb, the lined surface shown in FIG. 2 composed of materials 20 and 22 is placed against the skin and the strap encircles the limb with the end 32 of the strap overlapping section 16. When applied in that fashion, the Velcro strip 30 faces the looped fabric 17 of section 16 and the barbs of the Velcro engage the loops to releasably lock the ends together with the strap fairly tightly encircling the limb. Because section 14 is stretchable, the attendant can apply the strap 10 with sufficient tension so that the limb is firmly gripped by the band and held in place but without applying so much pressure to the limb as to cut off circulation. Further, because the Velcro 30 may be attached to any portion of section 16, the diameter of the encircling band is infinitely adjustable between the maximum expanded length of the strap and the relaxed length of section 14. That is, Velcro section 30 may essentially overlap the entire length of section 16 except the very end 34 which supports clip 42 described fully below.

While primary strap 10 is bound about the limb of the patient, secondary strap 12 made of a male Velcro-type fastening material is used to anchor the tube T in place. The secondary strap 12 may be approximately one inch wide and three inches long. One end 40 of strap 12 is threaded through the opening or eye of clip 42 so as to completely encircle one side 44 of the clip. The end 40 of strap 12 holding clip 42 is sewn to the surface of looped fabric material 17 where section 16 overlaps the end 46 section 14. The strip 12 is secured in that fashion with its barbs facing in the direction of section 16 as viewed in FIGS. 3 and 4. Thus, the unbarbed surface 48 of strip 12 faces the arm 44 of clip 42, and the barbs on the material are in face-to-face contact with the looped material 17 of section 16 where the strip is sewn to the overlapped ends of the primary strap 10. It is evident in the drawing that the free end 50 of secondary strap 12 may be threaded through the eye 52 of clip 42 under the arm 54 to form a closed loop from strap 12. As viewed in FIGS. 1 and 4, the end of the strip 12 extending beyond clip 42 may be secured firmly to the looped material 17 so as to releasably lock the secondary strap 12 in place. The clip 42 enables the strap 12 to be tightened firmly and uniformly about the tube T without flattening or pinching the tube, and then it may be locked merely by applying the barbed surface of end 50 to the looped material.

From the foregoing description it will be apparent that the band may readily be applied to the patient and will continue to function effectively so long as it is not intentionally disturbed. Unlike the prior art devices known to applicant, the tube T supported by the secondary strap will not readily loosen because the size of the loop encircling the tube is fixed and the force of the strap 12 on tube T is uniform about its circumference. And clip 42 makes it difficult to separate the strip from section 16 except by pulling upwardly from free end 50. That is, the size of the closed loop cannot readily be enlarged by pulling the strip from the closed end. To enlarge the size of the loop encircling tube T, the end 50 must be lifted from the material 16 and only after the locking action of the barbs and loops is completely broken can the strip be unthreaded from clip 42 to release tube T.

In FIGS. 5-8, the preferred embodiment of this invention is shown. This embodiment differs from that shown in FIGS. 1-4 only in the arrangement of the secondary strap. The primary strap is the same. The primary strap 60 includes the elasticized section 62 made of an elastic webbing material and the non-stretchable section 64 which correspond precisely to the sections 14 and 16 of the embodiment described above. The two sections are stitched together at their overlapped ends 66.

The secondary strap 70 composed of a Velcro band 72 and clip 74 are stitched to the primary band at the overlapped section 66 in somewhat different fashion than in the first described embodiment. It will be noted in FIG. 7 that the band 72 has its end 76 looped about one side 78 of the clip 74, and the major portion of the strap 72 is oriented so that its male barbs of the Velcro material face downwardly in face to face relationship with the looped material 80 that forms the female Velcro fastener for the primary strap 60. And in the rest or unused position (FIG. 5) the strap 72 extends in the direction of the section 64 rather than section 62 as in the first described embodiment.

Figure 7:
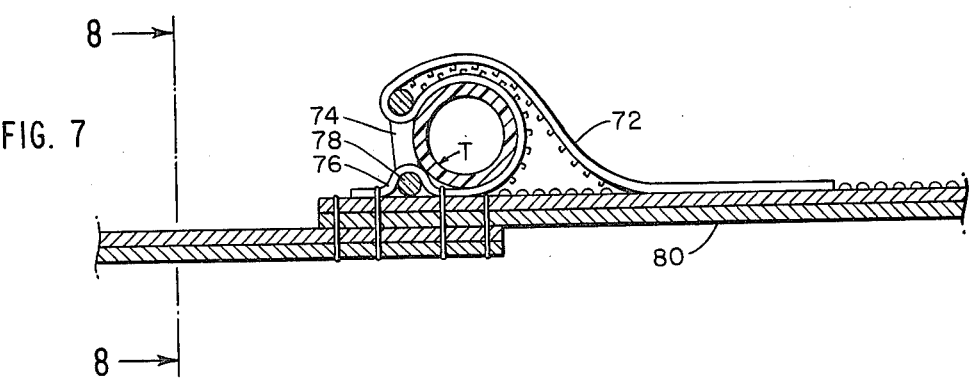
FIGS. 7 and 8 are cross sectional views taken along corresponding section lines in FIGS. 6 and 7.
Figure 8:
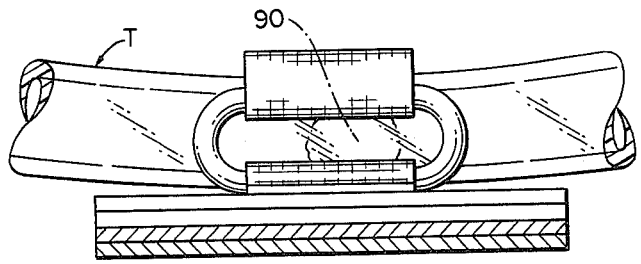

When the secondary strap 70 is used to retain the catheter tube T in place, the end 82 of the secondary band is inserted through the clip 74 after passing about the catheter tube T, and the strap thereafter is pulled in the direction over the section 64 of the primary strap so that the clip 74 turns up on its anchored arm 78. In this manner, the eye or opening of the clip as shown in FIG. 7 exposes the side of the catheter tube so that it is clearly visible. And the barbs of the male Velcro material on the secondary strap 72 are disposed in face to face relationship with the female material 80 and the secondary strap is thereby anchored in place.

In addition to the several advantages described above attributed to the first described embodiment, the preferred embodiment of this invention shown in FIGS. 5-8 has several additional advantages. First, because the strap 72 does not cover the entire catheter drainage tube T, the tube may be visually inspected through the eye of the clip while the tube is locked in place by the secondary strap 70. Therefore any occlusion in the tube as suggested at 90 in FIG. 8 may readily be detected by visual inspection without unlocking the tube assuming of course that the tube is transparent. Yet another advantage of this invention is the firm lock which is provided on the catheter tube by the clip. In this embodiment, the clip itself is drawn tightly against the tube and locks it firmly in place. This firm grip on the tube enables the attending nurse or doctor to apply tension to the catheter, sometimes called "catheter traction," which prevents crimping of the drainage tube that would adversely effect its operation. The firm grip on the tube also discourages the patient from removing or pulling at the catheter when in place in the urinary tract, which patients ordinarily have a tendency to do.

From the foregoing description, those skilled in the art will appreciate that modifications may be made of this invention without departing from its spirit. Therefore, we do not intend to limit the scope of this invention to the two embodiments illustrated and described. Rather, it is intended that the scope of this invention be determined by the appended claims and their equivalents.

What is claimed is:

1. A band for anchoring a catheter or other tubular device to the body comprising;
    an extendible primary strap adapted to encircle the portion of the body to which the device is to be anchored,
    fastening means connected to the primary strap for securing it in place on the body,
    a secondary strap means made of a flexible material and having a length less than the length of the primary strap,
    means for connecting one end of the secondary strap means to the primary strap intermediate the ends of the primary strap,
    a relatively rigid clip having an eye through which another end of the secondary strap means may be threaded to form a loop for encircling the device,
    means for securing the clip to the primary strap adjacent the one end of the secondary strap means and thus fixed with respect to said one end,
    and additional fastening means at the other end of the secondary strap means for retaining the end through the eye with the loop tightly bound about the device.

2. A band as described in claim 1 further characterized by said secondary strap means at least in part comprising a Velcro-type fastener, said Velcro fastener being the additional fastening means.

3. A band as described in claim 2 further characterized by said secondary strap means being made of male Velcro-like fastening material, and said primary strap at least in part being made of a soft looped material cooperating with the male Velcro fastening material to retain the secondary strap means through the eye.

4. A band as described in claim 1 further characterized by said primary strap including a length of soft looped material forming part of the additional fastening means.

5. A band as described in claim 4 further characterized by said primary strap also including a section of male Velcro-type fastening material forming part of the first recited fastening means together with the looped material.

6. A band as described in claim 5 further characterized by said secondary strap means including a section of male Velcro-type fastening material and forming part of the additional fastening means.

7. A band as described in claim 5 further characterized by said secondary strap means being made of a length of male Velcro-type fastening material.

8. A band as described in claim 7 further characterized by said secondary strap means being secured at one end to the primary strap, said end of the secondary strap also being fixed to the clip for retaining the clip on the primary strap.

9. A band as described in claim 8 further characterized by said clip having a pair of parallel arms, one of said arms being encircled by said one end of the secondary strap means which in turn is stitched to the primary strap, said secondary strap means being secured so that the major portion of its length has its male Velcro-type fasteners facing the looped material of the primary strap and extending in the direction of the looped material.

10. A band as described in claim 9 further characterized by said clip overlying a portion of the tubular device and retaining the device in position when the secondary strap means is inserted through the clip and fastened in face to face relationship with the looped material of the primary strap so that the tube may visually be inspected through the eye of the clip.

11. A band as described in claim 1 further characterized by, said additional fastening means including mating fastening members, one at the other end of the secondary strap means and the other on the facing surface of the primary strap.

12. A band as described in claim 11 further characterized by, said primary strap at least in part made of a soft looped material and said secondary strap means at least in part made of male Velcro-like fastening material cooperating with the looped material to retain the secondary strap means through the eye.

13. A band as described in claim 11 further characterized by said fastening member on said primary strap being disposed along the primary strap adjacent the one secured end of the secondary strap means and on the opposite side of the one secured end to the clip.

* * * * *